United States Patent
Mulholland et al.

(10) Patent No.: US 7,267,670 B2
(45) Date of Patent: Sep. 11, 2007

(54) REINFORCED URETHRAL SUPPOSITORY

(76) Inventors: S. Grant Mulholland, 1783 Sheeder Mill Rd., P.O. Box 20, Birchrunville, PA (US) 19421-0020; Paul Zupkas, 5197 Alta Vista St., San Diego, CA (US) 92109

( * ) Notice: Subject to any disclaimer, the term of this patent is extended or adjusted under 35 U.S.C. 154(b) by 0 days.

(21) Appl. No.: 09/943,380

(22) Filed: Aug. 30, 2001

(65) Prior Publication Data

US 2003/0050612 A1 Mar. 13, 2003

(51) Int. Cl.
*A61M 31/00* (2006.01)

(52) U.S. Cl. .................. 604/517; 604/285; 604/286; 604/287; 604/288

(58) Field of Classification Search ........ 604/512–517, 604/93.01, 187, 264–270, 273–279, 523, 604/544, 518, 519, 520, 19, 329, 330, 286–288, 604/48, 285
See application file for complete search history.

(56) References Cited

U.S. PATENT DOCUMENTS

| | | | | | |
|---|---|---|---|---|---|
| 1,537,992 | A | * | 5/1925 | Gearon ........................ | 604/288 |
| 1,767,785 | A | * | 6/1930 | De Sushko ................. | 604/288 |
| 3,126,887 | A | * | 3/1964 | Gordon ........................ | 604/288 |
| 4,460,360 | A | * | 7/1984 | Finegold ..................... | 604/288 |
| 4,542,020 | A | * | 9/1985 | Jackson et al. ............... | 514/31 |
| 5,085,650 | A | * | 2/1992 | Giglio ......................... | 604/288 |
| 5,482,039 | A | * | 1/1996 | Place ......................... | 600/407 |
| 5,919,474 | A | * | 7/1999 | Place et al. ................. | 424/430 |
| 5,981,593 | A | * | 11/1999 | Scott .......................... | 514/573 |
| 6,270,789 | B1 | * | 8/2001 | Sameshima et al. ......... | 424/433 |
| 6,291,528 | B1 | * | 9/2001 | Scott .......................... | 514/573 |
| 6,416,779 | B1 | * | 7/2002 | D'Augustine et al. ...... | 424/430 |
| 6,464,670 | B1 | * | 10/2002 | Mulholland ................. | 604/288 |
| 6,645,201 | B1 | * | 11/2003 | Utley et al. .................. | 606/41 |

FOREIGN PATENT DOCUMENTS

WO WO 00/13721 3/2000

OTHER PUBLICATIONS

Amemiya, T. et al., Development of emulsion type new vehicle for soft gelatin capsule. I. Selection of surfactants for development of new vehicle and its physical chemical properties., Chemical and Pharmaceutical Bulletin, Feb. 1998, 46(2):309-13.
Duckett, JW et.al., Intravesical morphine analgesia after bladder surgery., Journal of Urology, Apr. 1997, 157(4):1407-9.
Campbell's Urology., Edited by Walsh, PC et al., W.B. Saunders and Company, Six Edition, 1992.
D. Rosato and D. Rosato, editors, *Injection Molding of Plastics*, New York: Van Nostrand Reinhold, 1986.
P. Cracknell, editor, *Handbook of Thermoplastic Injection Mold Design*, New York: Blackie Academic and Professional, 1993.
I. Rubin, *Injection Molding; Theory and Practice*, New York: Wiley, 1973.
*Molding Systems*, Michigan: Society of Manufacturing Engineers, 1997.
R. Parnas, *Liquid Composite Molding*, Cincinnati: Hanser Gardner Publications, 2000.
A. Gennaro, editor, *Remington: The Science and Practice of Pharmacy*, 19th Edition, Easton: Mack Publishing Co., 1593, 1995.
B. Kemppanien and W. Reifenrath, editors, *Methods for Skin Absorption*, Boca Raton: CRC Press, 61, 1990.
V. Shah and H. Maibach, editors, *Topical Drug Bioavailability, Bioequivalence, and Penetration*, New York: Plenum Press, 369, 1993.

* cited by examiner

*Primary Examiner*—Ann Lam
(74) *Attorney, Agent, or Firm*—Catalyst Law Group, Apc; Michael B. Farber, Esq.

(57) ABSTRACT

A urethral suppository comprising a non-meltable base member sized to prevent insertion of the base member into the urethra, a non-meltable reinforcement projecting from the base member, and a meltable portion formed around a portion of the reinforcement. The meltable portion tapers along the reinforcement and is shaped for cooperating with the action of the periurethral musculature to retain the suppository within the urethra. A method of delivering one or more therapeutic agents to the female urinary tract, the method involving insertion of the urethral suppository into the urethra. A method for manufacturing a reinforced urethral suppository.

70 Claims, 10 Drawing Sheets

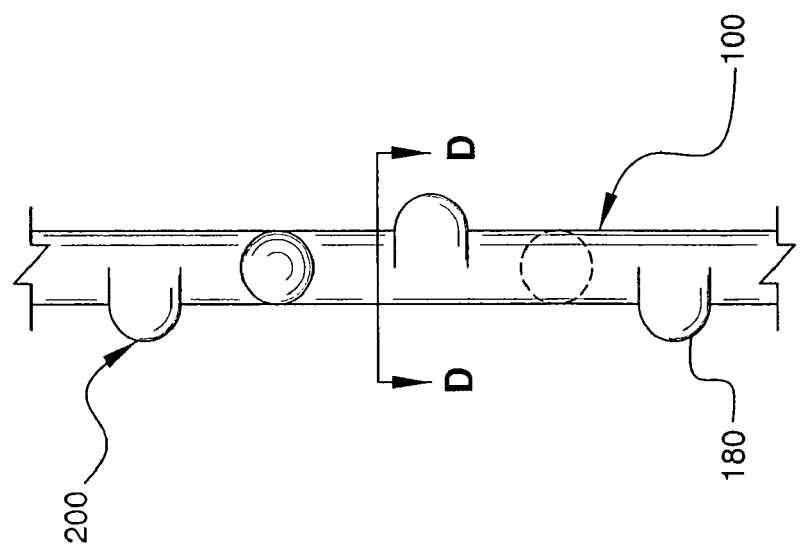
FIGURE 13
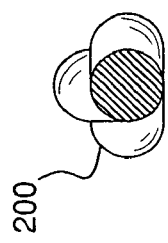
FIGURE 14
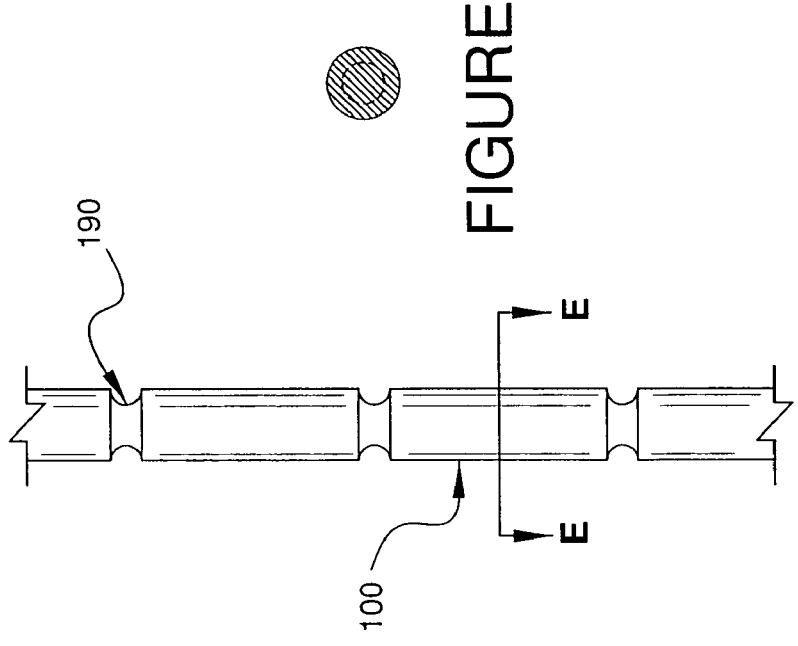
FIGURE 15
FIGURE 16

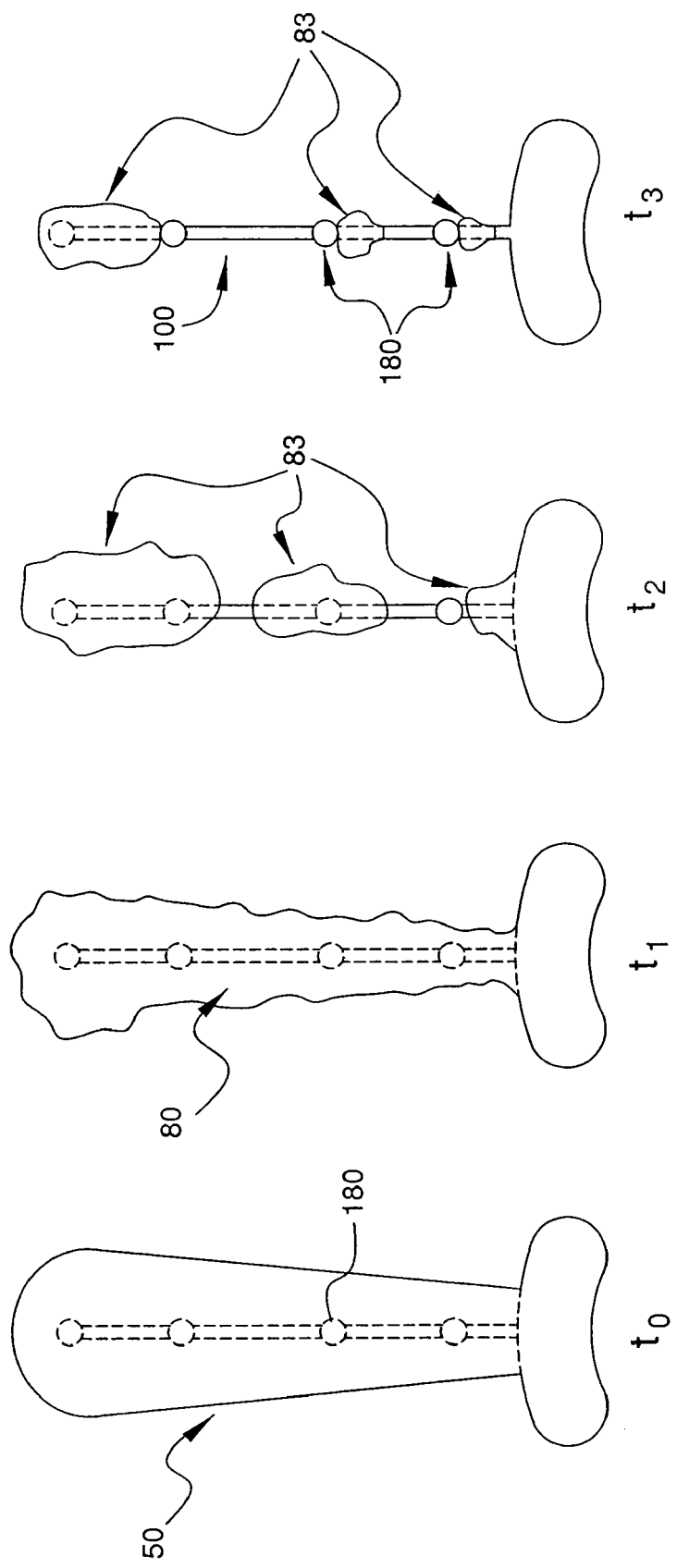

REINFORCED URETHRAL SUPPOSITORY

BACKGROUND OF THE INVENTION

Field of the Invention

This invention relates to a urethral suppository and methods of using it for delivering therapeutic agents to the urethra, bladder and related structures.

In the treatment of various ailments affecting the urethra, bladder and related structures, systemic delivery of therapeutic agents does not always give the most favorable clinical outcome.

Accordingly, it is known to employ suppositories as delivery devices for therapeutic agents. Such suppositories are designed to be inserted into the urethra and to release therapeutic agents contained therein or applied thereon to the mucosal lining of the urethra. The release of therapeutic agents occurs upon liquefaction of the suppository which results from the transfer to the suppository of the body heat of the patient into whose urethra the suppository has been placed (Amemiya, T.; et. al. Development of emulsion type new vehicle for soft gelatin capsule. I. Selection of surfactants for development of new vehicle and its physical chemical properties. Chemical and Pharmaceutical Bulletin, 1998, February 46(2): 309–13).

Nonetheless, it is of primary importance that the suppository is shaped for retention in the urethra, as well as having sufficient structural integrity so that upon insertion into the urethra, the suppository does not break, bend, or otherwise become misshaped.

Various prior art suppositories have been designed in such a manner that they are difficult to retain in position within the urethra where the precise delivery of therapeutic agents is desired. Experience has shown that such suppositories tend either to advance inwardly into the bladder or to be expelled out of the urethra prior to the complete liquefaction within the urethra. In either case, the desired result of a precise placement of the specific dosage of the selected therapeutic agents within the urethra is not realized.

In order to address these shortcomings, it is known to configure urethral suppositories in the form disclosed in U.S. Pat. No. 5,085,650 to Giglio (the '650 patent). The '650 patent discloses an urethral suppository comprising a bulbous head and a conical tail joined by a narrow cylindrical shaft. As taught by the '650 patent, upon insertion of the suppository into the urethra of a human female patient, the bulbous head thereof is advanced through the entire length of the urethra and penetrates into the bladder to anchor the suppository at the bladder neck. The conical tail of the suppository prevents the further advance of the suppository into the bladder. More specifically, once the suppository is positioned within the urethra, the portion of the bulbous head of the suppository which curves inwardly toward the shaft is designed to prevent the suppository from expulsion by its contact with the bladder walls at the bladder neck where the bladder narrows to the meet the proximal end of the urethra. At the same time, the flared portion of the conical tail, having an increasingly larger diameter than the shaft of the suppository as well as the urethra itself, is designed to prevent the suppository from over insertion by contact with the edges of the urethral orifice at the distal end thereof. It is through this combination of contact surfaces that the suppository disclosed in the '650 patent is intended to be held in position during the liquefaction thereof.

While suppositories configured with bulbous heads, conical tails and narrow cylindrical shafts, as disclosed in the '650 patent aid in the placement and retention of suppositories within the urethra as compared with purely cylindrical suppositories that lack such features, such configurations permit, nonetheless, some slippage and, moreover, present certain other disadvantages. Because retention of the suppository is effected, in part, by the contact between the inwardly curved portion of the bulbous head with the bladder neck, it is required that the bulbous head of the suppository advance beyond the urethra and invade into the bladder itself. As a result, where therapeutic agents are infused throughout the material comprising the suppository, the portion of the dosage contained within the material comprising the bulbous head thereof is not positioned so that it is in direct physical contact with the mucosal lining of the urethra and thus is not absorbed readily therein. As a result, the precise delivery of a specific dosage through absorption by the urethra cannot be realized effectively. Further, insofar as the conical tail section of the suppository disclosed in the '650 patent has a flat base, it is difficult to manipulate after insertion as it provides no projections which can be grasped readily. Moreover, the roundness of the conical tail renders the distal end of the suppository less than fully compatible with the anatomical structure of the labia. As a result, the comfort of the patient is compromised.

Mulholland (International Publication No. WO 00/13721) discloses a meltable suppository shaped to cooperate with the action of the periurethral musculature to retain the suppository within the urethra. The suppository has a shaft, the insertion end of which tapers toward a second end which comprises a knob sized to prevent insertion into the urethra. Nonetheless, the Mulholland device is formed only from meltable, malleable material which is subject to deformation when inserted into the urethra.

Any foreign body inserted into the urethra or bladder causes a degree of urgency, frequency, pain, and general discomfort to the patient. Medical devices, such as tubes, catheters, or instruments, commonly inserted in the bladder or urethra during urological procedures cause discomfort to patients (Duckett, J W; et. al. Intravesical morphine analgesia after bladder surgery. Journal of Urology, 1997, April 157(4): 1407–9; Campbell's Urology. Edited by Walsh, P C; et. al. W. B. Saunders and Company, Six Edition, 1992). This discomfort can become extreme when the device contacts the sensitive tissue of the bladder neck.

The bladder neck is a highly vascularized and innervated tissue containing specialized cells that play an important role in the voiding cycle. The bladder is very sensitive to pressure. Any foreign body within the bladder neck will cause major discomfort to the patient. Various prior art suppositories have been designed which do not take into consideration the effect of contacting the bladder neck with a portion of the suppository.

The present invention relates to the provision of a suppository for delivering a therapeutic agent to the urethra, the device designed to overcome the disadvantages of suppositories which buckling, break, or bend, or otherwise deform during insertion into the urethra; and suppositories or segments thereof formed from melting from migrating within the urethra or from exiting the urethra.

SUMMARY OF THE INVENTION

In accordance with one aspect of the present invention, there is provided a reinforced suppository, which possesses a non-meltable base member sized to prevent insertion of the base member into the urethra. Projecting from the base member is a non-meltable reinforcement. Formed around a length of the reinforcement is a meltable portion made from a material which is biocompatible and which comprises one or more therapeutic agents. The meltable portion has a diameter which tapers from the second end (insertion end) toward a first end, i.e. the end proximal to the base.

The meltable portion, inserted in the urethra, contains medication for delivery to body tissues over periods of time from minutes to hours. The base member facilitates handling, inserting and retaining of the meltable portion in the urethra, and fits comfortably against the urethral os. Preferred embodiments of the reinforced suppository include one or more restraints formed on the reinforcement. The restraints retard or prevent migration of the meltable portion as it melts into segments within the urethra.

In another aspect, the invention provides a reinforced urethral suppository for insertion into a female urethra in which a non-meltable base member has a surface which is sized to prevent insertion of said base member into said urethra. A non-meltable reinforcement, which has a length, a first end attached to the base, and a second end distal from the base projects from the base. The reinforcement has a urethral segment extending from the first end, and a bladder segment extending from the urethral segment. The bladder segments terminates in a reinforcement second end. The urethral and bladder reinforcement segments are sized such that the urethral segment is contained substantially entirely in the urethra, and the bladder segment is contained substantially entirely in the bladder, when the suppository is inserted into the female urethra. A meltable portion is formed around the entire length of the reinforcement. The meltable portion has a taper region formed around the reinforcement urethral segment, and an extension region formed around the reinforcement bladder segment. The taper region meltable portion has a diameter which tapers toward the reinforcement first end.

A further aspect of the invention provides a method for delivering one or more therapeutic agents to the female urinary tract. The method includes the steps of inserting a suppository of the invention into the urethra of a female patient, waiting a sufficient period for the suppository to deliver one or more therapeutic agents to the urinary tract, and removing the non-meltable reinforcement from the urethra.

Also provided herein is a method for manufacturing a reinforced urethral suppository. The method involves the steps of fabricating a single-unit comprising a non-meltable base member sized to prevent insertion of the base member into a female urethra, and a non-meltable reinforcement having a length, the length having a first end and a second end, the first end attached to and projecting from the base member. A further step involves forming a meltable portion having a distal end and a proximal end, the meltable portion having a diameter which tapers from the distal end to the proximal end. The meltable portion includes one or more therapeutic agents and a biocompatible material. Another step is directed to combining the non-meltable unit with the meltable portion whereby the meltable portion surrounds a portion of the length of the non-meltable reinforcement.

BRIEF DESCRIPTION OF THE DRAWINGS

FIG. 13 shows an embodiment of the reinforcement with restraints shaped as circular tab protrusions.

FIG. 14 is a cross sectional view of the reinforcement of FIG. 13, taken along line D—D.

FIG. 15 shows an embodiment of the reinforcement with restraints shaped as intrusions.

FIG. 16 is a cross sectional view of the reinforcement of FIG. 15, taken along line E—E.

FIGS. 17–20 show a time sequence of melting of the reinforced suppository into segments.

LIST OF ELEMENTS IN THE DRAWINGS

Figure 1:
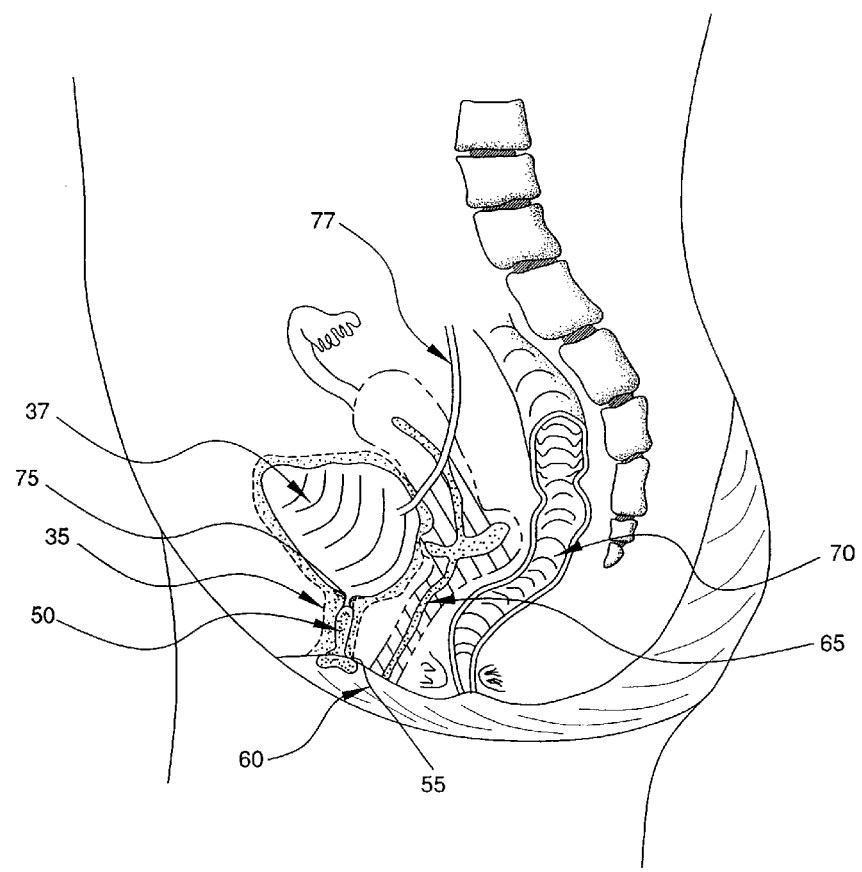
FIG. 1 shows a suppository of the invention inserted into the urethra, and related anatomical structures.

35—urethra
37—bladder
39—urethral wall
50—reinforced urethral suppository
55—urethral os
60—labia minora
65—vagina
70—rectum
75—bladder neck
77—ureter
80—meltable portion
83—segments of meltable portion
85—distal end of meltable portion
87—distal region of meltable portion
90—first end (proximal end) of meltable portion
95—base member
100—reinforcement
105—axis of ellipsoidal shape
110—surface of lower mid-section of base member
115—radial diameter of base member
120—first (proximal) end of reinforcement
125—distal end of reinforcement
130—oversized reinforcement
135—extension region of meltable portion
137—reinforcement bladder segment
140—diameter of distal region of meltable portion
141—reinforcement urethral segment
142—reinforcement second end
143—taper region of meltable portion 145—diameter of proximal end of meltable portion
150—longitudinal grooved configuration
155—peak
160—valley
165—grooves
170—corkscrew shape
175—helical groove
180—restraint
185—triangular protrusion
190—intrusion
195—rectangular protrusion
200—circular tab protrusion

DETAILED DESCRIPTION OF THE INVENTION

The reinforced suppository of the present invention is described with reference to International Publication No. WO 001/13721, which is hereby incorporated by reference.

Definitions

As used herein, the term "leak point pressure" refers to the pressure in the bladder required to overcome the opening pressure of the urethra and cause urine to escape from the bladder. In the female human, the opening pressure of the urethra is a result of a combination of the action of the pelvic floor levator muscles, elastic tissues, and an ill defined muscle group similar to the external sphincter muscle in the male urethra. The maximum pressure generated along the length of the urethra is typically at a point one third of the length of the urethra from its external opening. The pressure within the bladder must overcome this maximum pressure to cause urine to leak. The normal range for leak point pressures in the human female is 30–40 mm Hg.

As used herein, the term"structural support" means the ability of a body to resist deforming as a result of external forces acting on its surfaces.

As used herein, the term "melt" means to be changed from a solid to a liquid state (i.e. undergo liquifaction) by the application of heat, pressure, or both. When installed in the urethra, the meltable portion of the suppository invention undergoes liquifaction.

As used herein, the term "integrity" means the ability the meltable portion to maintain its position as it changes shape, melting and breaking into one or more segments, when external forces act to cause the meltable portion to migrate.

As used herein, the "lower urinary tract," refers to one or more organs, muscles and passageways that participate in the excretion of urine, in particular, the bladder, urethra, periurethral musculature, urethral os, and related structures.

The present invention is a reinforced urethral suppository that forms a drug delivery system for delivery of agents, either therapeutic or diagnostic, into the urethra or bladder of a female human. In one aspect, the invention provides medication in sufficient doses to treat afflicted tissues.

In one embodiment of the present invention, a urethral suppository generally designated (50) is shown inserted into a urethra (35) in FIG. 1. As shown in more detail in FIG. 2, the suppository comprises a non-meltable base member (95), sized to prevent insertion of the base member into the urethra. A meltable portion (80) is formed around a length of a non-meltable reinforcement that projects from the base member. The meltable portion tapers from distal end (125) of the reinforcement to the base member. After insertion, as the meltable portion melts, the reinforcement maintains the integrity of the meltable portion (80) until the meltable portion substantially liquefies during drug delivery. The reinforcement provides structural support to the suppository (50) as it is inserted into the urethra. It is understood that drug delivery involves contact of the melted or liquified melted portion with a target tissue, including, but not limited to, the urethral walls and related structures such as the bladder.

Figure 2:
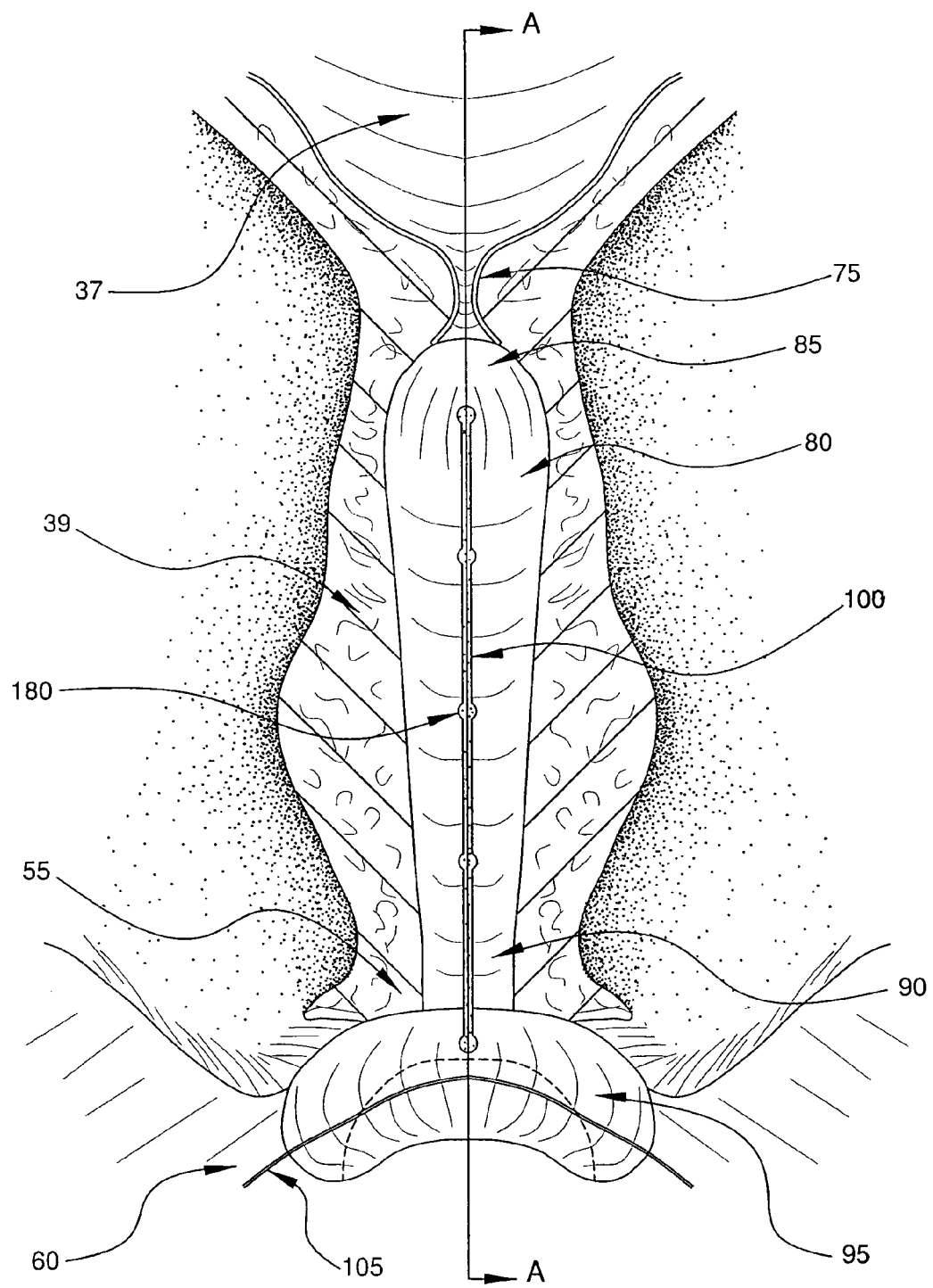
FIG. 2 shows a reinforced suppository of the invention inserted into the urethra, and illustrating the base member's ellipsoidal shape.
Figure 3:
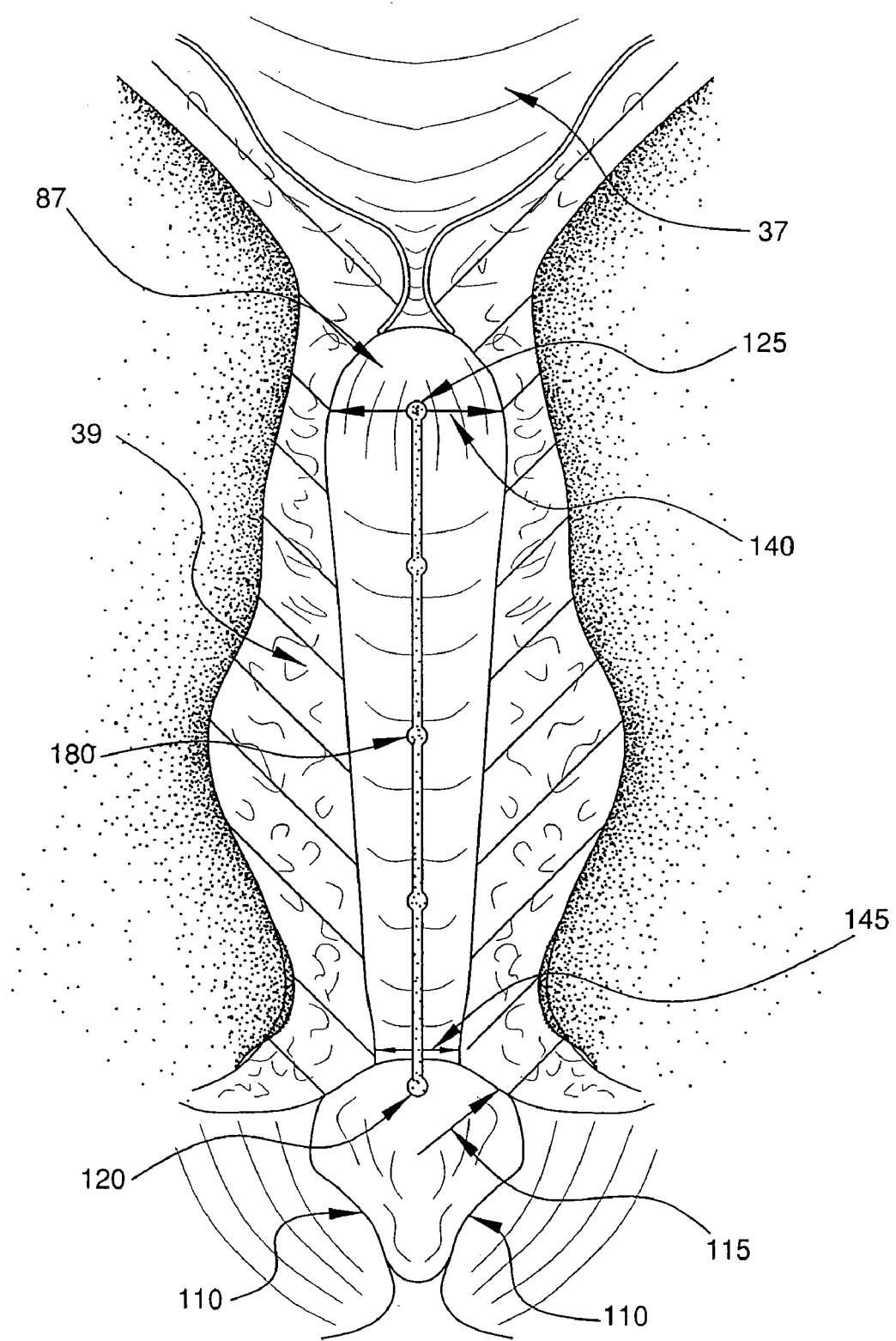
FIG. 3 shows a sectional view of the reinforced suppository of FIG. 2, taken along line A—A.

Referring to FIGS. 2 and 3, a preferred embodiment of the urethral suppository of the invention (50) is shown positioned in the urethra (35) of a female patient with the distal end (85) of the meltable portion in close proximity to, but not contacting the bladder neck (75); and base member (95) in contact with the urethral os (55) in the labia minora (60).

Base Member

The base member is adapted to fit comfortably juxtaposed to the urethral os (55). The base member is sized to prevent insertion of the base member into the urethra, thereby assuring proper positioning of the suppository in the urethra, and preventing the suppository from migrating into the bladder (37) as the suppository melts. In a sense, the base member functions as an anchor that prevents the suppository from migrating into the bladder analogously to an anchor which prevents a ship from drifting with the currents. The base member is preferably shaped for the user to grasp the suppository without touching the able portion (80). Contacting the meltable portion with the skin is undesirable as it can result in contamination or melting of the meltable portion. The shape of the base member must allow the user to comfortably manipulate the suppository into position in the urethral os (55) and sustain the necessary force to achieve insertion of the suppository in the urethra.

The base member (95) may be formed in various formats from a variety of materials depending on the needs of the user. The base member may be formed of a material that is rigid or flexible so long as it does not melt at a temperature equal to or less than that of the meltable portion. Preferred embodiments of the reinforced suppository are those in which the base member does not melt. A wide range of materials may form the base member, including, but not limited to, polyethylene, polypropylene, polyurethane, polyvinyls, silicone rubbers, nylons, cellulose, or other natural or synthetic materials. The base member may be of any thickness desired to suit the comfort of the patient and fulfill a functional requirements of the reinforced suppository, which is to prevent the suppository from migrating into the bladder.

Base member shapes may be formed by molding or other processes such as casting, extrusion, cutting, sawing, scribing, laser scribing, shearing, or otherwise forming the base member into the desired size or shape depending on the needs of the user. The base member can be formed into a broad range of geometric planar configurations circumscribed as polygonal, circular, and free form. A typical geometric shape is a curved ellipsoidal shape with no edges or corners that might cause patient discomfort or irritation (FIGS. 2 and 3).

Preferably, the axis (105) of the ellipsoidal shape is convex towards the urethral os (55) to maximize the length of the meltable portion (80) inserted into the urethra (35). The length of the curved axis (105) shown in FIG. 2 is in the range of about 15–30 mm with an optimal range of about 20–25 mm. The surfaces (110) of the lower midsection of the ellipsoid shown in FIG. 3 are concave to permit the suppository to be grasped between the forefinger and thumb. Additionally, the surfaces (110) of the lower mid-section of the ellipsoid may be grooved and/or roughened to improve traction and prevent or limit the suppository from slipping during handling. The radial diameter (115) of the base member (95) is in the range about 6–9 mm, preferably about 7–8 mm.

Reinforcement

As shown in FIG. 2, the reinforcement (100) projects from the base member (95). The proximal end (120) of the reinforcement, which is otherwise attached to the base member, is either embedded in or contiguous with the base member. The reinforcement has a dual function. First, it provides structural support to the suppository during the insertion process preventing the meltable portion from breaking or buckling. Secondly, it provides integrity to the suppository during the drug delivery phase by acting as an anchor for the meltable portion of the suppository and segments thereof within the urethra.

Forces acting on the surface of the meltable portion during insertion can be resolved into a combination of forces parallel and perpendicular to the axis of the portion of the suppository inserted in the urethra. The forces parallel to the axis will cause the portion of the suppository inserted in the urethra to compress against the base member during insertion. The forces perpendicular to the axis will cause the portion of the suppository inserted in the urethra to bend or buckle. If the bending or buckling exceeds the plastic limit of the combination of the meltable portion and the reinforcement, it will break. Therefore, the suppository, and particularly the portion of the suppository inserted in the urethra, must possess sufficient structural support to overcome these parallel and perpendicular forces to achieve insertion.

The materials of fabrication, and the design dimensions of the meltable portion and reinforcement will greatly effect the structural support of the suppository. In choosing fabrication materials or design dimensions for the meltable portion or reinforcement, consideration must be given to factors such as solubility of the therapeutic agent in the base material of the meltable portion and rate of liquifaction of the meltable portion. However, with these factors in mind, the combination of the reinforcement and meltable portion must provide sufficient structural support to the suppository to achieve insertion. Therefore, if the meltable portion is formed from a soft and pliable material, such as a gelatine, the reinforcement should be formed from a material that provides a high degree of rigidity. If the meltable portion is formed from a rigid material, such as a glycerin or polypropylene, the reinforcement may be formed from a material that possesses a lower degree of rigidity or even a flexible material, such as a thread or suture. A wide range of materials may form the reinforcement, including, but not limited to, polyethylene, polypropylene, polyurethane, polyvinyls, silicone rubbers, nylons, cellulose, or other natural or synthetic materials.

Dimensions of the meltable portion and the reinforcement also affect the structural support of the suppository. The diameter of the reinforcement is in the range of about 0.5 to about 2 mm with a preferable range of about 1 to about 1.5 mm. It is desirable for the reinforcement to have a small diameter while providing the highest degree of structural support to the suppository. The properties of the material used to fabricate the reinforcement may require a compromise between the diameter and the degree of rigidity. Increasing the diameter of the reinforcement, increases its rigidity and improves the structural support of the portion of the suppository inserted in the urethra. However, the size of the suppository inserted in the urethra is constrained by issues of patient tolerability and pain. Therefore, increasing the diameter of the reinforcement, reduces the amount of meltable portion making up the total volume of the portion of suppository inserted in the urethra. Reducing the volume of the meltable portion is undesirable as it limits the amount and profile of drug delivery. In contrast, if a very small diameter, or in the extreme, no reinforcement is used in the suppository, the meltable portion must possess sufficient rigidity on its own to overcome the opening pressure of the urethra and the external forces acting on its surface during the insertion process. The requirement for rigidity in the meltable portion limits the choices for fabrication materials. Materials with sufficient rigidity may not possess optimal properties for mixing with therapeutic agents or melting at desired rates.

Maintaining the integrity of the meltable portion and its position within the urethra is also an important function of the reinforcement. As the shape of the meltable portion tapers towards the base member, there is less meltable material. Therefore, sections of the meltable portion closer to the base member will completely melt faster than distal sections, assuming all other factors remain the same. Variations in the pressure of the urethra acting on the meltable portion will also cause it to melt at different rates along its length during the drug delivery phase. The result of these factors is the meltable portion will melt into segments (83) before it has entirely melted. Most likely, the last segments to melt will be those segments distal to the base member this is shown in FIGS. 17–20.

In the absence of a reinforcement, segments (83) of the meltable portion shown in FIGS. 19 and 20 that detach from the base member (95) are free to migrate as a result of forces generated within the urethral wall (39) as described above. The reinforcement is shaped to prevent or limit the distance these segments (83) migrate. The reinforcement anchors the meltable portion along its entire length, thereby preventing segments (83) of the meltable portion from moving as they become detached from the base member.

Embodiments of the reinforcement involve shapes that maintain the integrity of the meltable portion and keep segments (83) of the meltable portion in position within the urethra. A reinforcement can be configured as a rod, a ratchet, from parts or elements which include, but are not limited to rod, ratchet, umbrella, and cone, i.e. shapes onto which the meltable portion is formed. The shapes can be solid, hollow, or combinations of meshes and lattices which otherwise provide sufficient structural support and integrity. In a preferred embodiment, the reinforcement is a rod with restraints (180) formed along its length to prevent or limit the meltable portion or segments thereof from moving in a longitudinal direction. FIGS. 17–20 show a time sequence of the meltable portion melting into segments, while the reinforcement and restraints (180) inhibit or prevent the movement or migration of the meltable portion and segments thereof.

Referring to FIGS. 17–20, a reinforced suppository (50) before insertion and the start of melting or liquefaction is shown at time $t_0$. After insertion, the suppository (50) changes shape as the meltable portion (80) begins to melt, shown at time $t_1$. As the meltable portion continues to melt, it breaks into segments (83) as shown at time $t_2$. Migration of these segments (83) along the reinforcement (100) is limited or prevented by the presence of restraints (180) on the reinforcement (100) as shown at time $t_3$.

Figure 4:
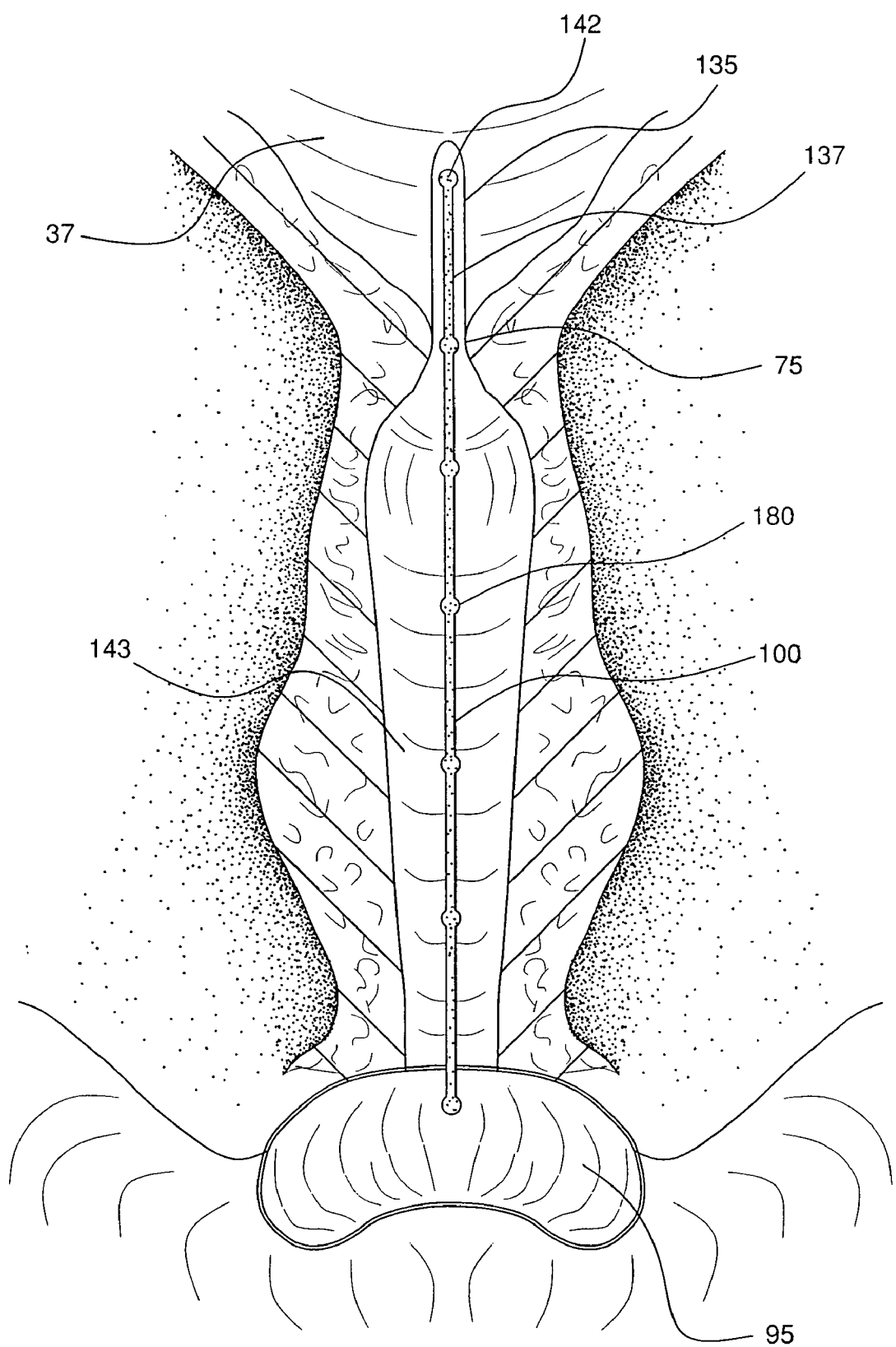
FIG. 4 shows an embodiment of a reinforced suppository in which a bladder segment of the reinforcement is surrounded by meltable material and extends into the bladder.
Figure 6:
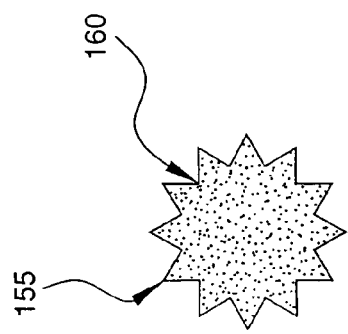
FIG. 6 is cross sectional view of the suppository meltable portion of FIG. 5, taken along line A—A.
Figure 9:
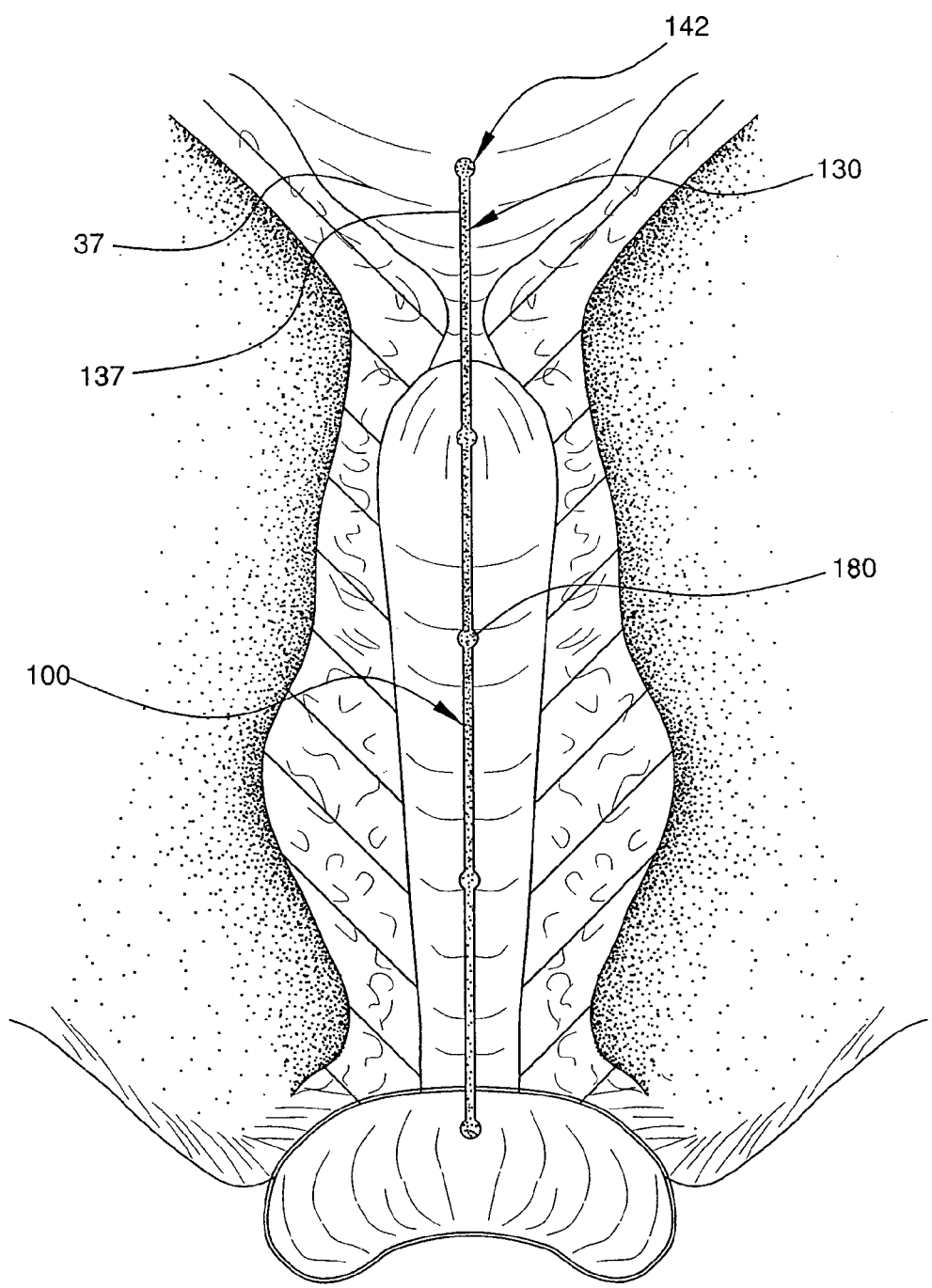
FIG. 9 shows an embodiment of the reinforced suppository in which the distal portion of the reinforcement extends into the bladder.
Figure 12:
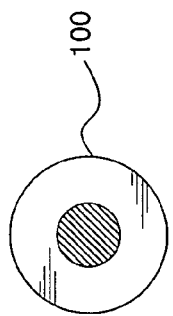
FIG. 12 shows a cross sectional view of the reinforcement of FIGS. 10 and 11, taken along line C—C.
Figure 11:
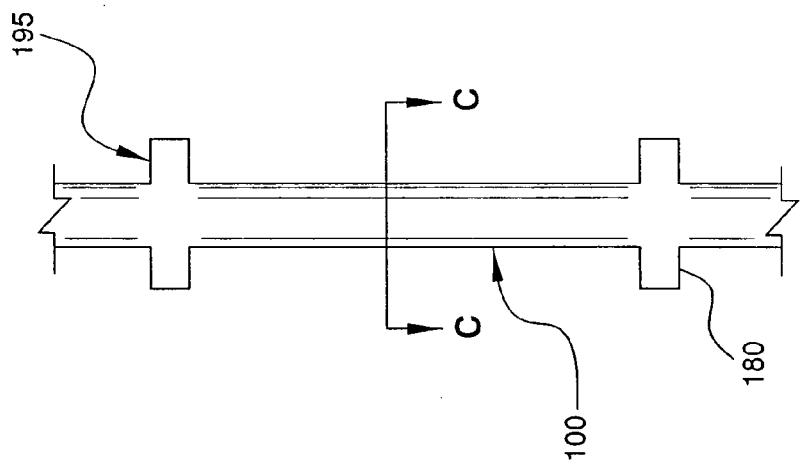
FIG. 11 shows an embodiment of the reinforcement with restraints shaped as rectangular protrusions.
Figure 10:
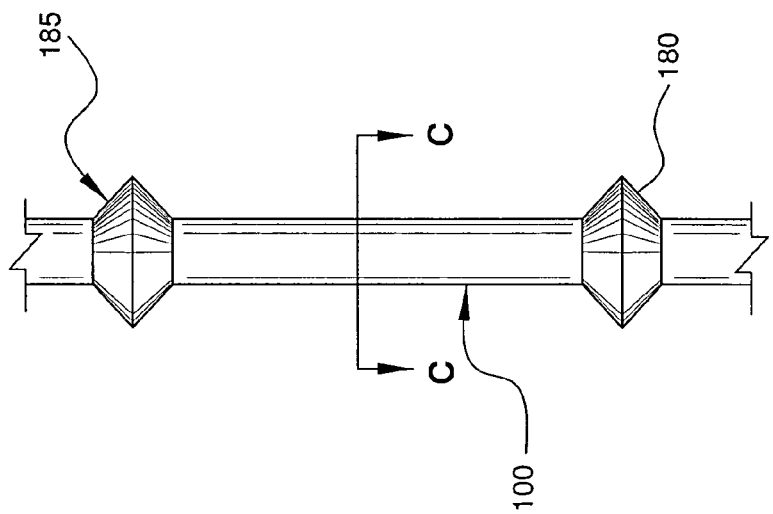
FIG. 10 shows an embodiment of the reinforcement with restraints shaped as triangular protrusions.

The length of reinforcement (100) may vary depending on the clinical needs of the user. In one embodiment, the distal end (125) of the reinforcement may terminate within the distal region (87) of the meltable portion (80) making the length of the reinforcement slightly less than the length of the meltable portion (See FIG. 2). In the case where the meltable portion is contained entirely in the urethra, the length of the reinforcement will be in the range of about 25 to about 40 mm. In another embodiment, as shown in FIGS. 4 and 9, the distal end (125) of the reinforcement may extend into the bladder (37) to create an oversized reinforcement (130), which may act as a wick for the liquefied meltable portion to flow into the bladder (37). The diameter of the portion of suppository (135) extending into the bladder (37) is significantly less than the diameter of the distal end (85) of the meltable portion to limit or prevent contact with the sensitive tissue of the bladder neck and urethral sphincter. In a preferred embodiment, the diameter of the extended length of the meltable portion (135) extending into the bladder (37) would be no greater than twice the diameter of the reinforcement. In all cases, the length of the reinforcement ranges between about 25 to about 80 mm. The appropriate length of reinforcement, meeting the clinical and structural needs of the suppository, (50) is routinely determined by one of skill in the art.

Meltable Portion

The meltable portion of the suppository of the invention comprises a biocompatible carrier medium formed around a length of the reinforcement. In certain embodiments (FIG. 9) the reinforcement extends beyond the distal end (85) of the meltable portion. As disclosed above, the biocompatible carrier medium suitable for use in the suppository of the present invention may be selected from any of a wide variety of biocompatible materials which are capable of being combined with the desired therapeutic agents at a desired dosage.

The meltable portion of the suppository of the invention can vary in length according to the needs of the user. The length of the adult female urethra is about 3 to about 4.5 cm. Any contact with, and irritation to the sensitive area of the bladder neck (75) (FIG. 1) will yield a sense of urgency in the female patient. Therefore, a preferable length of the meltable portion is about 2.5 to about 4.5 cm, with a more preferable range of about 3.0 to about 4.0 cm. However, in certain circumstances where it is desirable to provide medication to the bladder (37), the length of the meltable portion can be greater than 4.5 cm.

Referring to FIG. 4, the extended length (135) of the meltable portion should be formed in a manner that minimizes contact with the bladder neck, but provides access to the bladder. As shown, extending from the base member, a non-meltable reinforcement has, a first end (90) attached to the base and a second end distal (142) from the base. A urethral segment of the reinforcement (141) extends from the first end and a bladder segment (137 extends from said urethral segment. The bladder segment terminates in a reinforcement second end (142). The urethral and bladder reinforcement segments sized such that the urethral segment is contained substantially entirely in the urethra, and the bladder segment is contained substantially entirely in the bladder, when the suppository is inserted into the female urethra. A meltable portion is formed around the entire length of said reinforcement. The meltable portion has a taper region (143) formed around the reinforcement urethral segment and an extension region (135) formed around the reinforcement bladder segment. The taper region meltable portion has a diameter which tapers toward the reinforcement first end.

A preferable maximum diameter (140)(FIG. 3) of the distal region (87) of the suppository meltable portion (80) is in the range of about 5 mm to about 12 mm, with a more preferable range of about 6 mm to about 9 mm. In some cases, the diameter of the embodiments of the invention may be more than 12 mm according to clinical requirements. For diameters larger than 12 mm, the patient would typically require anesthesia to reduce the pain and discomfort of insertion. The anesthetic could be applied topically to the urethra prior to insertion or incorporated into the meltable portion. The diameter (145) at the proximal end of the meltable portion is in the range of about 3 mm to about 10 mm with a preferable range of about 4 mm to about 7 mm. See FIG. 3.

Figure 5:
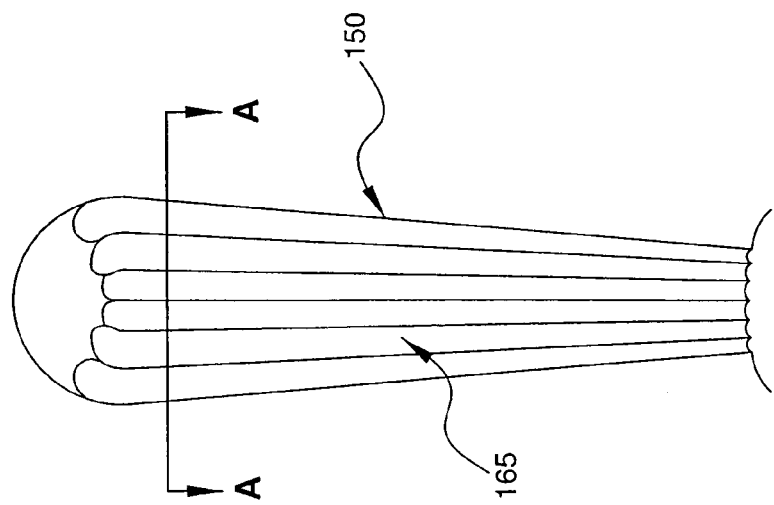
FIG. 5 is an embodiment of the meltable portion of the suppository; the meltable portion has longitudinal grooves.
Figure 8:
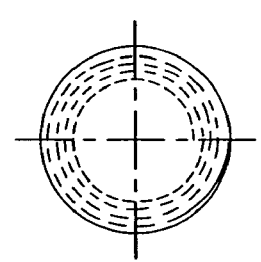
FIG. 8 is a cross sectional view of the suppository meltable portion of FIG. 7, taken along line B—B.

Embodiments of the suppository meltable portion may assume a broad range of geometric configurations. A preferable axial cross-section is circular. However, other configurations possess desirable functional characteristics relating to drug delivery or treatment modality. Referring to FIG. 5, by means of example and not limitation, one such configuration has a longitudinal grooved configuration (150), with an axial cross-section of peaks (155) and valleys (160) running all or part of the length of the meltable portion. This shape allows the melted suppository to constantly bath the tissue of the urethral wall (39)(FIG. 2) by providing grooves (165) for melted therapeutics to flow through.

Figure 7:
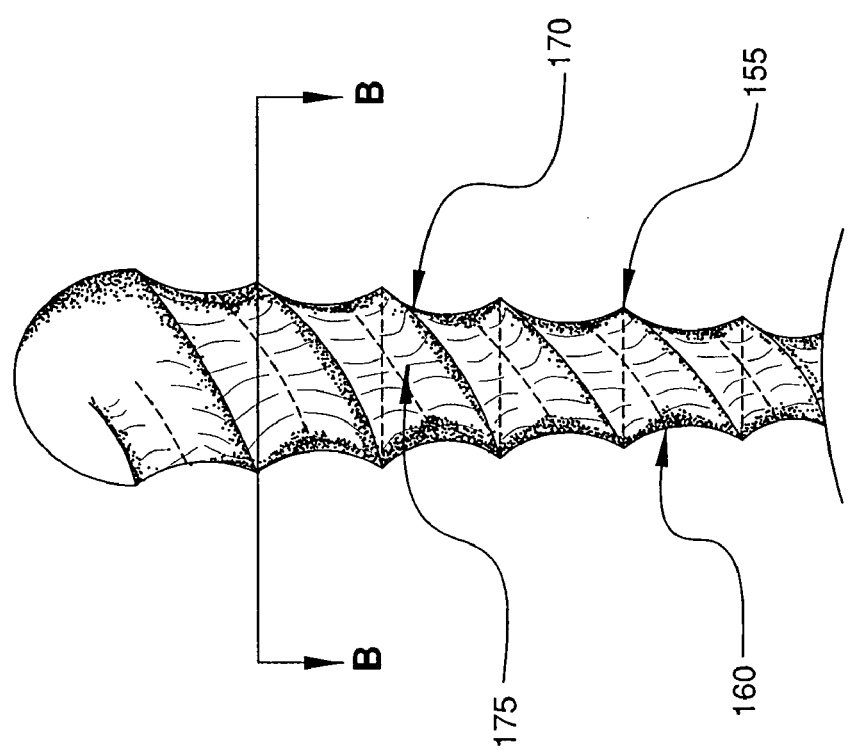
FIG. 7 shows an embodiment of the meltable portion which has helical peaks and valleys formed on the surface.

Referring to FIG. 7, by means of another example and not limitation, a second configuration of the suppository meltable portion involves a corkscrew shape (170), with one or more helical grooves (175) running part of or the entire length of the meltable portion. The corkscrew shape creates a similar structure by which the melted suppository constantly bathes the tissue of the urethral wall (39). However, the valley (160) created by the helical groove creates a continuous channel allowing the liquefied suppository to flow to any position along the length of the meltable portion.

The melting time of the suppository meltable portion depends on the physical and chemical properties of the biocompatible carrier medium combined with the therapeutic agent. The quantity of biocompatible carrier medium will affect the melting time, as the melting time is proportional to the quantity of biocompatible carrier medium. Higher molecular weight materials in the biocompatible carrier medium will also affect the suppository melting point. As an example, a suppository composed of 1000 molecular weight polyethylene glycol (PEG) would require refrigeration to prevent melting, while adding 4000 molecular weight PEG would result in a more heat stable suppository. In the present invention, the range of melting points would allow for suppositories to melt over periods as short as about one minute for anesthetizing the urethra to about ten hours to provide therapeutic relief to an incontinent patient.

Restraints

A preferred embodiment of the present invention further comprises restraints (180) formed along the length of a rod-shaped reinforcement (100). As described above, and as shown in FIGS. 17–20, the suppository meltable portion breaks or melts into segments (83) within the urethra as a result of variation in urethral pressure on the tapered shape of the meltable portion (80). The restraints, which in one embodiment comprise round or bulbous protrusions (180) (FIGS. 2 and 3) on the reinforcement (100) prevent or limit the movement of the segments of the meltable portion as they melt within the urethra. Maintaining the position of the meltable portion or segments thereof optimizes the amount of therapeutic agents exposed to the surface of the urethral wall (39), and therefore is critical to maximizing effects of the therapeutic agents. Additionally, migration of the segments of the meltable portion out of the urethra will reduce the amount of time therapeutic agents are in contact with the urethral wall, and thus limit the absorption of the therapeutic agents into the urethral tissue.

Embodiments of restraints (180) on the reinforcement (100) comprise a broad range of geometric shapes and configurations, including but not limited to protrusions and intrusions. A reinforcement may comprise a combination, i.e. one or more shapes of restraints. Additionally, there can be one or a plurality of restraints (180) on the reinforcement.

A preferred embodiment of a geometric shape for a restraint is a small hemispherical protrusion formed around the longitudinal axis of the reinforcement (100). Referring to FIGS. 10–16, other shapes include, but are not limited to protrusions and intrusions. Shapes of protrusions or intrusions include but are not limited to triangles, rectangles, spheres, hemispheres, ellipses, plates, and rods.

In choosing a shape for a restraint, it should be remembered that sharp edges or corners scrapping against the urethral wall during removal of the reinforcement may result in irritation or injury to the urethra. The restraints of the invention include any shape of a restraint that prevents, resists, or limits movement or migration of segments of the softened meltable portion, while not causing discomfort or irritation to the patient.

Fabrication of the Reinforced Suppository

The suppository base member and reinforcement are inexpensively and easily fabricated by molding or extrusion processes. An artisan's choice of a method of fabricating the reinforced suppository of the invention is guided by functional design elements for a particular therapeutic use or set of uses of the invention. Methods include but are not limited to injection molding, blow molding, compression molding, heat forming, or other forms of molding or extrusion processes well understood by those knowledgeable in the arts of fabricating plastic materials. Depending on the functional or clinical requirements of the reinforced suppository, the base member and reinforcement can be fabricated as a single unit, or as individual elements by different processes and combined in an assembly step into a single unit, or in series using insert molding techniques. See D. Rosato and D. Rosato, editors, *Injection Molding of Plastics*, New York: Van Nostrand Reinhold, 1986; P. Cracknell, editor, *Handbook of Thermoplastic Injection Mold Design*, New York: Blackie Academic and Professional, 1993; I. Rubin, *Injection Molding; Theory and Practice*, New York: Wiley, 1973; *Molding Systems*, Michigan: Society of Manufacturing Engineers, 1997; R. Parnas, *Liquid Composite Molding*, Cincinnati: Hanser Gardner Publications, 2000.

Methods of making the suppository of the invention include separate fabrication of the base member and the reinforcement. The first end of the reinforcement is attached to the base member in an assembly step using adhesives, mechanical attachment, or other suitable means for achieving a secure and functional attachment. In this embodiment, the base member may be fabricated from a soft and pliable plastic to reduce irritation and discomfort to the patient. The reinforcement may be fabricated from a harder material that provides the necessary rigidity to the meltable portion (80) and structural support to the suppository (50) for insertion into the urethra.

In another embodiment the base member and reinforcement are fabricated as a single unit by any of the above molding and extrusion fabrication methods. This embodiment requires selection of a material that balances patient comfort with providing rigidity to the meltable portion and structural support to the suppository.

The final step in the fabrication of the present invention is forming the meltable portion around the reinforcement. In another embodiment, the meltable portion is formed as a solitary unit followed by the insertion of the combined base member/reinforcement unit into the meltable portion, as a final assembly step. The meltable portion comprises a mixture of one or more therapeutic agents and a meltable biocompatible material. One of skill in the art will select the process by which the meltable portion is formed onto the reinforcement. Processes include, but are not limited to injection molding or compression molding the meltable portion into the desired shape. See A. Gennaro, editor, *Remington: The Science and Practice of Pharmacy*, 19$^{th}$ Edition, Easton: Mack Publishing Co., 1593, 1995; B. Kemppanien and W. Reifenrath, editors, *Methods for Skin Absorption*, Boca Raton: CRC Press, 61, 1990; V. Shah and H. Maibach, editors, *Topical Drug Bioavailability Bioequivalence, and Penetration*, New York: Plenum Press, 369, 1993.

The practice of the invention is illustrated by the following non-limiting examples.

EXAMPLE 1

Oxybutynin Suppository

An oxybutynin suppository formulated for slow melting is fabricated by injection molding and/or insert molding a meltable portion onto a previously fabricated reinforcement and base member placed in cavities of a suppository mold. The meltable portion is formed from the ingredients in Table 1 below according to the following steps.

1. Weigh oxybutynin and dissolve in an appropriate volume of sterile water.
2. Add parabens to dissolved oxybutynin solution while stirring.
3. Add the gelatine and glycerin to dissolved oxybutynin solution and stir to a homogenous mixture.
4. Allow the homogenous mixture (the meltable portion) to sit for four hours and then heat to 65° C. while rigorously stirring.
5. Heat PEG 1500 to 65° C. and add to homogeneous meltable portion mixture while stirring vigorously.
6. Stir meltable portion mixture at 65° C. at slow speed to remove all air bubbles.
7. Place the previously formed base and reinforcement in their respective cavities in the suppository mold.
8. Inject the 65° C. bubble free meltable portion into the suppository mold. so as to form a meltable portion around a length of the reinforcement.
9. Cool molds to room temperature before separating mold halves and removing formed reinforced oxybutynin suppository.

TABLE 1

| Ingredient | Percent by weight |
| --- | --- |
| Gelatine | 24.81% |
| Sterile Water for Injection | 23.03% |
| Glycerin | 42.30% |
| PEG1500 | 9.33% |
| Oxybutynin | 0.35% |
| Methylparaben | 0.12% |
| Propylparaben | 0.06% |

EXAMPLE 2

Lidocaine Suppository

A lidocaine suppository formulated for slow-melting is fabricated by injection molding a meltable portion onto a previously fabricated reinforcement and base member placed in formed cavities of a suppository mold. The meltable portion is formed from the ingredients of Table 2, with the following steps.
1. Weigh lidocaine and dissolve in an appropriate volume of sterile water.
2. Add parabens to dissolved lidocaine solution while stirring.
3. Add the gelatine and glycerin to dissolved lidocaine solution and stir to a homogenous mixture.
4. Allow the homogenous mixture to sit for four hours and then heat to 65° C. while rigorously stirring.
5. Heat PEG 1500 to 65° C. to homogeneous mixture while stirring vigorously. This is the material which forms the meltable portion.
6. Stir meltable portion material at 65° C. at slow speed to remove all air bubbles.
7. Place the previously formed base and reinforcement in their respective cavities in the suppository mold.
8. Inject 65° C. bubble free meltable portion material into suppository mold. so as to form the meltable portion around a length of the reinforcement.
9. Cool molds to room temperature before separating mold halves and removing formed reinforced lidocaine suppositories

TABLE 2

| Ingredient | Percent by Weight |
| --- | --- |
| Gelatine | 24.83% |
| Sterile Water for Injection | 16.25% |
| Glycerin | 42.30% |
| PEG1500 | 9.33% |
| Oxybutynin | 7.11% |
| Methylparaben | 0.12% |
| Propylparaben | 0.06% |

EXAMPLE 3

Clinical Use of Oxybutynin Suppository

This example describes the benefits and function of an oxybutynin suppository of the invention in treating over active bladder. A female patient, 52 years old, is diagnosed with over active bladder, presenting twenty uncontrolled daily voiding episodes, sterile urine, and no bladder or urethral pain. Voiding episodes restrict her movements, requiring she never be more than a short distance from a toilet. Additionally, for fear of embarrassment due an uncontrolled voiding episode in a public gathering, she avoids places where she is around many people, such as restaurants, stores, movie theaters, etc. She attempts to manage her voiding using adult diapers, but is fearful they will not contain her volume of voided urine. Her doctor prescribes an anti-cholinergic agent, oxybutynin chloride, taken orally three times per day in 5 mg pills. Although the agent eliminates the uncontrolled voiding episodes, the woman develops severe dry mouth and dizziness associated with any activity. These side effects are so severe she is forced to discontinue medication.

Alternatively, her doctor prescribes an oxybutynin urethral suppository of the invention. Before leaving home, she opens the individually wrapped suppository, grasping it by the handle; she inserts the meltable portion, containing up to 5 mg of oxybutynin chloride, into her urethra. Waiting a few minutes to allow the meltable portion to liquefy and the oxybutynin to be absorbed into the urethral wall, the woman is now free to leave her home without fear of uncontrolled voiding. The meltable portion will completely liquefy over a period of about 30 minutes to about 2 hours, however, the effect of the medication will last 6 hours or more. If necessary, the woman can remove the remaining portions of the suppository and insert a new suppository to prevent uncontrolled voiding episodes. Because the medication is delivered topically to the urethral walls and absorbed directly into urinary tissue through the urethral wall, the side effects of the medication are greatly reduced or eliminated.

EXAMPLE 4

Clinical Use of a Lidocaine Suppository

This example describes the benefit and function of a lidocaine suppository of the invention to reduce the pain and discomfort during cystoscopic examination of the bladder. A female patient, 36 years old, complains of bladder pain and hematuria, blood in her urine. Her doctor's suspects she may have bladder cancer, but requires a cystoscopic visual inspection of the bladder wall, to confirm the diagnosis. Her doctor performs the examination using a 21 Fr. Storz 30° cystoscope with a 9 Fr. working channel to allow biopsy of any suspicious lesions in her bladder. The operation is performed in the doctor's office as an outpatient procedure.

In preparation for the procedure, the patient is placed on an examination table in the dorsal lithotomy position. This allows the doctor easy access to the patient's urethra as a means for accessing the bladder. The cystoscope, cabling, light source, camera, irrigating system, and other instruments to be used in the procedure are placed in close proximity to the examination table. The procedure is expected to take between 10–30 minutes and require manipulation of the cystoscope to view the lumenal surface of the bladder. The stretching of the urethral wall, the pressure on the urethra resulting from manipulating the cystoscope, and the and movement of the cystoscope back and forth in the urethra to access proximal and distal portion of the bladder will cause pain and discomfort to the patient. To avoid the need for general anesthesia and reduce patient pain and discomfort, the suppository of the invention comprising a topical anesthetic is inserted into the urethra prior to the procedure. This topical anesthetic is in the form of a 2% lidocaine suppository. The meltable portion of the suppository liquefies in about 2 to about 5 minutes, bathing the urethral walls with a lidocaine fluid that anesthetizes as well as lubricates the urethra for the duration of the procedure.

The present invention may be embodied in other forms without departing from the spirit or essential attributes thereof. Accordingly, reference should be made to the appended claims, rather than to the foregoing specification, as indicating the scope of the invention.

What is claimed is:
1. A urethral suppository for insertion into a female urethra, said suppository comprising:
   a. a non-meltable base member not for insertion into said urethra, said base member having a surface;

b. a non-meltable reinforcement having a length, said length having a first end and a second end, said first end attached to said base member and projecting from said base member; and c. a meltable portion formed around said length of said reinforcement, said meltable portion having a diameter which tapers from said reinforcement second end to said reinforcement first end such that the taper occupies substantially the extent of the meltable portion from the second end of the reinforcement to the first end of the reinforcement, said meltable portion for insertion into said urethra;

said base member having a width in one direction perpendicular to the reinforcement, which width is greater than the maximum width of the meltable portion in a direction perpendicular to the reinforcement.

2. The urethral suppository of claim 1 wherein said base member is shaped for handling by a user of said suppository.

3. The urethral suppository of claim 1 wherein the base member is grooved to facilitate handling by a user.

4. The urethral suppository of claim 1 wherein the surface of said base member is roughened to reduce slippage of suppository during insertion.

5. The urethral suppository of claim 1 wherein said base member is formed from one or more materials selected from the group consisting of synthetic polymer, urethane, cellulose, glass, metal, rubber, and cloth.

6. The urethral suppository of claim 1 wherein said reinforcement projects substantially perpendicular from said base member.

7. The urethral suppository of claim 1 wherein said reinforcement comprises a shape selected from the group consisting of ratchet, helix, cone and solid rod.

8. The urethral suppository of claim 7 wherein said shape is comprised of a lattice or mesh.

9. The urethral suppository of claim 1 wherein said reinforcement is formed from one or more materials selected from the group consisting of urethane, cellulose, glass, metal, rubber, and cloth.

10. The urethral suppository of claim 1 wherein upon insertion of the suppository into the urethra, the second end of said reinforcement is contained entirely within the meltable portion.

11. The urethral suppository of claim 1 wherein the length of said reinforcement is in the range of about 40.0mm to about 80.0mm.

12. The urethral suppository of claim 11 wherein said reinforcement has a diameter in the range of about 0.5mm to about 2.0mm.

13. The urethral suppository of claim 1 wherein said reinforcement comprises one or more restraints formed along the portion of the length of the reinforcement on which the meltable portion is formed.

14. The urethral suppository of claim 13 wherein said one or more restraints are selected from one or more of the group consisting of protrusions, intrusions, and combinations thereof.

15. The urethral suppository of claim 14 wherein said protrusions have shapes selected from the group of shapes consisting of spheres, hemispheres, triangles, rectangles, plates, rods, and combinations thereof.

16. The urethral suppository of claim 14 wherein said intrusions have shapes selected from the group of shapes consisting of spheres, triangles, rectangles, plates, rods, and combinations thereof.

17. The urethral suppository of claim 1 wherein said meltable portion comprises one or more materials selected from the group consisting of theobroma oil and modified theobroma oil products, glycerinated gelatin, hydrogenated vegetable oils, cellulose, poiy (vinyl alcohol), poly (vinylpyrrolidone), polyacrylamide, poly (ethylene glycol), poly (phospho urethanes), polyoxyl stearate and ethylenoxide polymers.

18. The urethral suppository of claim 1 wherein said meltable portion comprises one or more therapeutic agents selected from one or more of the group of agents consisting of antibiotics, antimicrobials, antifangals, analgesics, anesthetics, steroidal anti-inflammatories, non-steroidal anti-inflammatories, mucous production inhibitors, hormones, and antispasmodics.

19. The urethral suppository of claim 1 wherein the diameter of the meltable portion formed around the second end is in the range of about 5 to about 12 millimeters.

20. The urethral suppository of claim 1 wherein the diameter of the meltable portion formed around the first end is in the range of about 4 to about 10 millimeters.

21. The urethral suppository of claim 1 wherein grooves are formed in said meltable portion.

22. The urethral suppository of claim 21 wherein said grooves are parallel to a longitudinal axis of the meltable portion.

23. The urethral suppository of claim 21 wherein said grooves are helical.

24. The urethral suppository of claim 21 wherein said grooves form a passage for liquid melted from said meltable portion.

25. The urethral suppository of claim 1 wherein said meltable portion has a length greater than about 4.5cm.

26. The urethral suppository of claim 1 wherein the length of said meltable portion is from about 2.5 cm to about 5.0 centimeters.

27. The urethral suppository of claim 1 wherein said meltable portion melts within about 2 minutes to about 60 minutes.

28. The urethral suppository of claim 1 wherein said reinforcement has a length in the range of about 25.0mm to about 80.0mm.

29. The urethral suppository of claim 1 wherein the length of said reinforcement is in the range of about 25.0mm to about 40.0mm.

30. A urethral suppository for insertion into a female urethra, said suppository comprising:

a. a non-meltable base member not for insertion into said urethra, said base member having a surface;

b. a non-meltable reinforcement having a length, said length having a first end and a second end, said first end attached to said base member and projecting from said base member; and c. a meltable portion formed around at least a portion of said length of said reinforcement, said meltable portion having a diameter which tapers from said reinforcement second end toward said reinforcement first end such that the taper occupies substantially the extent of the meltable portion from the second end of the reinforcement to the first end of the reinforcement, said meltable portion for insertion into said urethra, said non-meltable base member being wider than the meltable portion, wherein said base member is an ellipsoid having a major axis substantially perpendicular to the longitudinal axis of the reinforcement.

31. The urethral suppository of claim 30, wherein said ellipsoid is curved to promote maximal penetration of the meltable portion in the urethra.

32. A urethral suppository for insertion into a female urethra, said suppository comprising:
   a. a non-meltable base member not for insertion into said urethra, said base member having a surface;
   b. a non-meltable reinforcement having a length, said length having a first end and a second end, said first end attached to said base member and projecting from said base member; and
   c. a meltable portion formed around at least a portion of said length of said reinforcement, said meltable portion having a diameter which tapers from said reinforcement second end toward said reinforcement first end, such that the taper occupies substantially the extent of the meltable portion from the second end of the reinforcement to the first end of the reinforcement, said meltable portion for insertion into said urethra, wherein said reinforcement first end is embedded within said base member, said non-meltable base member being wider than the meltable portion.

33. A urethral suppository for insertion into a female urethra, said suppository comprising:
   a. a non-meltable base member not for insertion into said urethra, said base member having a surface;
   b. a non-meltable reinforcement having a length, said length having a first end and a second end, said first end attached to said base member and projecting from said base member; and
   c. a meltable portion formed around at least a portion of said length of said reinforcement, said meltable portion having a diameter which tapers from said reinforcement second end toward said reinforcement first end, said meltable portion for insertion into said urethra, wherein said base member is an ellipsoid having a major axis substantially perpendicular to the longitudinal axis of the reinforcement, wherein the second end of said reinforcement extends outside the meltable portion.

34. A urethral suppository for insertion into a female urethra, said suppository comprising:
   a. a non-meltable base member not for insertion into said urethra, said base member having a surface;
   b. a non-meltable reinforcement having a length, a first end attached to the base and a second end distal from the base, said reinforcement projecting from the base and comprising a urethral segment extending from said first end and a bladder segment extending from said urethral segment and terminating in said reinforcement second end, wherein the urethral segment is contained substantially entirely in the urethra, and the bladder segment is contained substantially entirely in the bladder, when the suppository is inserted into the female urinary tract; and
   c. a meltable portion formed around the entire length of said reinforcement, said meltable portion comprising a taper region formed around said reinforcement urethral segment and an extension region formed around the reinforcement bladder segment, said taper region of the meltable portion having a diameter which tapers toward said reinforcement first end such that the taper occupies substantially the extent of the meltable portion from the second end of the reinforcement to the first end of the reinforcement;
   said base member having a width in one direction perpendicular to the reinforcement, which width is greater than the maximum width of the meltable portion in a direction perpendicular to the reinforcement.

35. The urethral suppository of claim 34 wherein said base member is shaped for handling by a user of said suppository.

36. The urethral suppository of claim 34 wherein the surface of said base member is grooved to facilitate handling by a user.

37. The urethral suppository of claim 34 wherein the surface of said base member is roughened to reduce slippage of the suppository during insertion.

38. The urethral suppository of claim 34 wherein said base member fits within the labia minora of a patient.

39. The urethral suppository of claim 34 wherein said base member is formed from one or more materials selected from the group consisting of synthetic polymer, urethane, cellulose, glass, metal, rubber, and cloth.

40. The urethral suppository of claim 34 wherein said reinforcement projects substantially perpendicular from said base member.

41. The urethral suppository of claim 34 wherein said reinforcement comprises a shape selected from the group consisting of ratchet, helix, cone and solid rod.

42. The urethral suppository of claim 41 wherein said shape is comprised of a lattice or mesh.

43. The urethral suppository of claim 34 wherein said reinforcement is formed from one or more materials selected from one or more of the groups consisting of urethane, cellulose, glass, metal, rubber, and cloth.

44. The urethral suppository of claim 34 wherein said reinforcement comprises one or more restraints formed along said length of said reinforcement.

45. The urethral suppository of claim 44 wherein said restraints are selected from one or more of the group consisting of protrusions and intrusions.

46. The urethral suppository of claim 45 wherein said protrusions are selected from one or more of the group of shapes consisting of spheres, hemispheres, triangles, rectangles, plates, and rods.

47. The urethral suppository of claim 45 wherein said intrusions are selected from one or more of the group of shapes consisting of spheres, hemispheres, triangles, rectangles, plates, and rods.

48. The urethral suppository of claim 34 wherein said meltable portion comprises one or more materials selected from the group consisting of theobroma oil and modified theobroma oil products, glycerinated gelatin, hydrogenated vegetable oils, cellulose, poly (vinyl alcohol), poly (vinylpyrrolidone), polyacrylamide, poly (ethylene glycol), poly (phospho urethanes), polyoxyl stearate and ethylenoxide polymers.

49. The urethral suppository of claim 34 wherein said meltable portion comprises one or more therapeutic agents selected from one or more of the group of agents consisting of antibiotics, antimicrobials, antifungals, analgesics, anesthetics, steroidal anti-inflammatories, non-steroidal anti-inflammatories, mucous production inhibitors, hormones, and antispasmodics.

50. The urethral suppository of claim 34 wherein the maximum diameter of the meltable portion formed around the urethral region is in the range of about 5 to about 12 millimeters.

51. The urethral suppository of claim 34 wherein the diameter of the meltable portion formed around the first end is in the range of about 4 to about 10 millimeters.

52. The urethral suppository of claim 34 wherein grooves are formed in said meltable portion.

53. The urethral suppository of claim 52 wherein said grooves are parallel to a longitudinal axis of the meltable portion.

54. The urethral suppository of claim 52 wherein said grooves are helical.

55. The urethral suppository of claim 52 wherein said grooves form a passage for liquid melted from said meltable portion.

56. The urethral suppository of claim 34 wherein the length of said taper region is from about 2.5 cm to about 5.0 centimeters.

57. The urethral suppository of claim 34 wherein upon insertion, said meltable portion melts within about 2 minutes to about 60 minutes.

58. The urethral suppository of claim 34 wherein the length of said reinforcement is in the range of about 40.0mm to about 80.0mm.

59. The urethral suppository of claim 58 wherein said reinforcement has a diameter in the range of about 0.5mm to about 2.0mm.

60. The urethral suppository of claim 34 wherein the length of said reinforcement is in the range of about 25.0mm to about 40.0mm.

61. A urethral suppository for insertion into a female urethra, said suppository comprising:
  a. a non-meltable base member not for insertion into said urethra, said base member having a surface;
  b. a non-meltable reinforcement having a length, a first end attached to the base and a second end distal from the base, said reinforcement projecting from the base and comprising a urethral segment extending from said first end and a bladder segment extending from said urethral segment and terminating in said reinforcement second end, wherein the urethral segment is contained substantially entirely in the urethra, and the bladder segment is contained substantially entirely in the bladder, when the suppository is inserted into the female urinary tract; and
  c. a meltable portion formed around the entire length of said reinforcement, said meltable portion comprising a taper region formed around said reinforcement urethral segment and an extension region formed around the reinforcement bladder segment, said taper region meltable portion having a diameter which tapers toward said reinforcement first end such that the taper occupies substantially the extent of the meltable portion from the second end of the reinforcement to the first end of the reinforcement, wherein said base member is an ellipsoid having a major axis substantially perpendicular to the longitudinal axis of the reinforcement.

62. The urethral suppository of claim 61, wherein said ellipsoid is curved to promote maximal penetration of the meltable portion in the urethra.

63. A method for delivering one or more therapeutic agents to the female urinary tract, said method comprising the steps of: a. inserting a urethral suppository into the urethra of a female patient; b. waiting a sufficient period for said suppository to deliver one or more therapeutic agents to said urinary tract; and c. removing the non-meltable reinforcement from the urethra;
  wherein the urethral suppository comprises a non-meltable base member not for insertion into said urethra, said base member having a surface; a non-meltable reinforcement having a length, said length having a first end and a second end, said first end attached to said base member and projecting from said base member; and a meltable portion formed around said length of said reinforcement, said meltable portion having a diameter which tapers from said reinforcement second end toward said reinforcement first end such that the taper occupies substantially the extent of the meltable portion from the second end of the reinforcement to the first end of the reinforcement, said meltable portion for insertion into said urethra, said non-meltable base member being wider than the meltable portion.

64. The method of claim 63 wherein the period ranges from about 1 minutes to about 10 hours.

65. The method of claim 63 wherein the period ranges from about 2 minutes to about 2 hours.

66. The method of claim 63 wherein said insertion step comprises grasping the suppository by the non-meltable base member, and positioning the suppository into the urethra wherein the base member sits completely within the labia minora.

67. A method for delivering one or more therapeutic agents to the female urinary tract, said method comprising the steps of: a. inserting a urethral suppository into the urethra of a female patient; b. waiting a sufficient period for said suppository to deliver one or more therapeutic agents to said urinary tract; and c. removing the non-meltable reinforcement from the urethra;
  wherein the urethral suppository comprises a non-meltable base member not for insertion into said urethra, said base member having a surface; a non-meltable reinforcement having a length, a first end attached to the base and a second end distal from the base, said reinforcement projecting from the base and comprising a urethral segment extending from said first end and a bladder segment extending from said urethral segment and terminating in said reinforcement second end, wherein the urethral segment is contained substantially entirely in the urethra, and the bladder segment is contained substantially entirely in the bladder when the suppository is inserted into the female urinary tract; and a meltable portion formed around the entire length of said reinforcement, said meltable portion comprising a taper region formed around said reinforcement urethral segment and an extension region formed around the reinforcement bladder segment, said taper region meltable portion having a diameter which tapers toward said reinforcement first end such that the taper occupies substantially the extent of the meltable portion from the second end of the reinforcement to the first end of the reinforcement, said non-meltable base member being wider than the meltable portion.

68. The method of claim 67 wherein the period ranges from about 1 minutes to about 10 hours.

69. The method of claim 68 wherein the period ranges from about 2 minutes to about 2 hours.

70. The method of claim 67 wherein said insertion step comprises grasping the suppository by the non-meltable base member, and positioning the suppository into the urethra wherein the base member sits completely within the labia minora.

* * * * *